United States Patent [19]

Yiv

[11] Patent Number: 4,975,468

[45] Date of Patent: Dec. 4, 1990

[54] FLUORINATED MICROEMULSION AS OXYGEN CARRIER

[75] Inventor: Seang H. Yiv, Wilmington, Del.

[73] Assignee: Affinity Biotech, Inc., Malvern, Pa.

[21] Appl. No.: 331,713

[22] Filed: Apr. 3, 1989

[51] Int. Cl.$^5$ ............................................. A61K 31/02
[52] U.S. Cl. ..................................................... 514/759
[58] Field of Search ......................................... 514/759

[56] References Cited

U.S. PATENT DOCUMENTS 4,443,480 4/1984 Clark ..................................... 514/772

Primary Examiner—Mukund J. Shah
Assistant Examiner—C. L. Cseh
Attorney, Agent, or Firm—J. Edward Hess; Donald R. Johnson

[57] ABSTRACT

A fluorocarbon microemulsion is provided which contains an ethoxylated alcohol as surfactant, the alcohol containing a tertiary carbon atom.

5 Claims, No Drawings

FLUORINATED MICROEMULSION AS OXYGEN CARRIER

BACKGROUND OF INVENTION

This invention relates to a new surfactant for perfluorocarbon (PFC) microemulsions.

PFC emulsions are well known and have great promise as blood substitutes and other medical applications. Several properties critical to the success of a PFC emulsion are primarily due to the specific surfactant employed. For example, the emulsion must be stable so that it can be stored for long periods, preferably for many months and at room temperature. If the emulsion particles agglomerate during storage, or in the worst case the emulsion separates, there is no means in most hospitals for re-emulsifying it to the original condition. Although factors such as the specific PFC and the amount of PFC contribute to emulsion stability, the stability is largely determined by the surfactant.

Additionally, the emulsion particles must be sufficiently small to pass through the smallest capillaries without plugging them. Current thinking is that the PFC particles should be smaller than 0.2 micron, preferably less than 0.1 micron. Although the ultimate particle size achievable depends somewhat on the energy input in the emulsification step, it depends mainly on the specific emulsifier employed.

In respect of stability and particle size, the emulsion ideally is a microemulsion. Microemulsions behave as solutions i.e., as a single phase. They are well known in the enhanced oil recovery art and have achieved some recognition in PFC emulsions. See, e.g., U.S. Pat. No. 3,989,843 to Pierre Chabert et al. Such emulsions can be formed with relatively mild agitation and are stable for months over a specified temperature range. Above or below this range, the emulsion will deteriorate into two phases, but if returned to the specified temperature range they revert to the stable microemulsion form upon such mild agitation as hand shaking. Ideally, the range of temperature stability encompasses the intended use which for internal medical application is about 18°-43° C., i.e., from slightly below room temperature to the temperature of a high fever.

Another necessary emulsion characteristic is the obvious overriding requirement of any medical composition that it be non-toxic. The toxicity or lack of toxicity of a PFC emulsion is attributable in large part to that of the surfactant, since the preferred fluorocarbons described above show very minimal toxicity. The surfactant toxicity is generally unpredictable and bears little relationship to its emulsification ability. Some, such as the amine oxides, make outstanding emulsions from a strictly technical standpoint, but are quickly ruled out, nonetheless, because of their generally high toxicity.

There are other important in vivo characteristics of a PFC emulsion. One is the tendency of the emulsion to not cause crenation of the red blood cells. Crenation is a change in the shape of these cells from generally circular to a horned or starry shape. The latter cells do not pass through the arteries as well. Ideally, the PFC emulsion does not cause any crenation, or at least limits it to a short duration, e.g., less than 30 minutes.

A further in vivo attribute is lack of aggregation of the PFC particles in the emulsion. This refers to the tendency of the particles, in the presence of blood, to form clusters of particles. Although this gathering into clusters is distinct from the phenomenon where several particles merge into a single larger particle, the clusters have most of the same disadvantages; they increase the emulsion viscosity, and they also do not traverse the arteries as well.

Another necessary attribute is that the emulsion not cause hemolysis, which is a deterioration of the red blood cell membrane with an attendant loss of hemoglobin.

DESCRIPTION OF THE PRIOR ART

U.S. Pat. Nos. 3,911,138 and 4,105,798 are typical of the prior art principally directed to the use of PFC emulsions as oxygen transport agents in medical applications. The surfactant used in the early work was most often a polyoxyethylene exemplified by the "Pluronics" (Wyandotte Chemical) but as work progressed it was found that the Pluronics were not low enough in toxicity, because of their propensity to cause complement activation, and did not make an emulsion of adequate stability.

U.S. Pat. No. 4,461,717 was a successful attempt to improve emulsion stability by the use of amine oxide surfactants. Although a significant step forward, the emulsions of this patent do not have the characteristically good qualities of microemulsions and, in addition, the emulsion toxicity still leaves much room for improvement.

U.S. Pat. No. 3,989,843, to Pierre Chabert et al, is one the early PFC microemulsion patents. This patent discloses the ability to make PFC microemulsions by using a mixture of fluorinated surfactants of a specific formula, namely

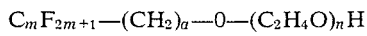

$$C_mF_{2m+1}-(CH_2)_a-O-(C_2H_4O)_nH$$

where m=4-10, a=1-4, and n=1-5 for one component of the surfactant mix and 6-40 for the other.

Unfortunately, the emulsions of this patent still have too high a toxicity. See Medecine et Armees, Paris 1984, 12/2, which reports work done at the University of Nancy, France, with the ether-type surfactants described by the above formula. They were said to have "proved to be very toxic." Id. at page 105.

SUMMARY OF THE INVENTION

We have found that by making a critical change in surfactants of the general type described above in Chabert et al, a substantially non-toxic PFC microemulsion can be made which has substantially all of the attributes described above as necessary and/or desirable in PFC emulsions.

Specifically, we have found that if a tertiary carbon atom is disposed between the fluorinated alkyl chain and alkylene oxide chain, a remarkable and surprising improvement in emulsion physical properties is obtained.

DETAILED DESCRIPTION OF THE INVENTION

The perfluorocarbon in the emulsion is generally a perfluorocyclocarbon, i.e., a cyclic compound of carbon which may or may not contain acrylic or alkyl side chains. The compound may be mono, di or polycyclic, as with cyclohexane or the perhydro derivatives of naphthalene and phenanthrene but usually has no more than 4 rings, preferably 2-3. The description of the cyclocarbon as perfluoro means that at least 75%, preferably at least 90%, more preferably at least 99%, of the hydrogen atoms have been replaced with fluorine. For effective use as a blood substitute the cyclocarbon usually has 9–12 carbon atoms.

Typical compounds of the type described above are perfluoro trimethylcyclohexane, isopropylcyclohexane, tetramethylcyclohexane, 1-methyl-4-isopropylcyclohexane, n-butylcyclohexane, decahydroacenaphthene, decalin, methyl and dimethyldecalins, tetradecahydrophenanthrene, dodecahydrofluorene, and diisopropylcyclohexane.

Preferred cyclocarbons are non-aromatizable polycyclic perfluoro compounds having two bridgehead carbon atoms linked through a bridge containing at least one carbon atom. By the term "bridgehead carbon atom" is meant a carbon atom bonded to three other carbons in a cyclic compound having 2 or more rings. By the term "non-aromatizable" is meant a polycyclic perfluoro compound whose ring structure cannot be aromatized without destruction of its original carbon-to-carbon cyclic bonds.

These preferred compounds are distinguished from perfluorodecalin and others mentioned above which can be aromatized. Examples of these preferred compounds are the perfluoro derivatives of such $C_9$–$C_{12}$ polycyclic compounds as bicyclononanes (e.g. bicyclo[3.3.3]nonane, 2,6-dimethylbicyclo[3.3.1]nonane or 3-methylbicyclo-[3.3.1]nonane), adamantane, methyl and dimethyladamantane, ethyladamantane, tetrahydrodicyclopentadiene, methyl and dimethylbicyclooctanes, pinane, comphane, 1,4-6,9-dimethanodecalin, bicyclo[4.3.2]undecane, bicyclo[5.3.0]- decane and the like, or mixtures thereof. They can be made by known means. Compounds of this preferred type are described in U.S. Pat. No. 4,105,798 which is incorporated herein by reference.

Certain acyclic perfluorocarbons have also been used, or evaluated for use, in medical applications, most notably perfluorotributylamine, perfluorooctane, 1,1,2-trihydroper fluoro-1-decene, 1,1,1,2-pentahydroperfluorodecane and the like.

The aqueous phase of the emulsion is water alone but often it will be a saline solution isotonic with blood such as Ringer's or Tyrode's solution. It may, if desired, also contain a therapeutic agent such as any of the drugs described in U.S. Pat. No. 4,742,050 the disclosure of which is incorporated herein by reference.

The surfactants of our invention have the following structure:

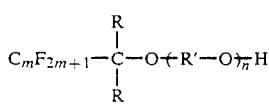

where m is 4–12, n will be in the range of 5–30, but will have an average value ($\bar{n}$) of 5–20, preferably 7–13, each R is independently selected from $C_{1-5}$ alkyl and fluoroalkyl and R' is $C_2H_4$ or $C_3H_6$ or both. Preferably m is 6–10, R is $C_{1-3}$ alkyl or fluoroalkyl, more preferably $CF_3$ or $CH_3$, and R' is $C_2H_4$.

As will be described below the surfactant is usually a combination of a more hydrophilic component with a "high" n and a less hydrophilic component with a "low" n. The average n is the weighted average of all the different values of n in the entire surfactant composition.

The tertiary carbon atom shown in the above formula is essential to achieving a surfactant of the properties we describe. The adjacent Rs are preferably alkyl, e.g., $CH_3$, because the precursor (e.g., acetone) is easier to make than the $CF_3$ precursor (hexafluoroacetone). However, if it is an alkyl such as $CH_3$, then $C_m$ is generally 2–3 carbon atoms longer in order to get equivalent surfactant properties than when R is $CF_3$. So in this respect R is preferably fluoroalkyl.

The factors involved in making our microemulsions are several, but it is not difficult to make the appropriate determinations based on the guidelines and examples presented below.

One factor is the amount of PFC. Large amounts tend to require larger amounts of surfactant. Normally the amount of PFC is 10–50% (by volume of total emulsion), preferably 10–30%. The surfactant will usually be 1–10% (w/v, i.e., gms surfactant/100cc emulsion) and is preferably 2–5%.

Another factor is the value of n. In order to better describe this relationship, the nature of our microemulsions should be clarified. Microemulsions generally exist, i.e., remain a single phase and act as a solution, over a specific temperature range. Outside of this range they become cloudy because two visible phases have formed. These two phase systems are not microemulsions since, as noted above, one of the characteristics of microemulsions is that they look and act as a single phase.

The effect of n can be seen as follows. In the discussion which follows the emulsions referred to are prepared in the following manner.

The surfactant and PFC are added to a glass container followed by saline solution to 100cc total. The saline solution is 0.9%(w/v). The amounts of the other components are as specified. The PFC is methyladamantane (MA) or dimethyladamantane (DMA), as specified, each also having bicyclononanes present. These materials are as described in U.S. Pat. No. 4,105,798. In the surfactant, each R is $CF_3$ and m is 6. The value of n is as specified. The container is shaken while the ingredients are added, and as the mixture is then heated to 80° C. The mixture is cooled to room temperature and a clear, bluish, single phase microemulsion is obtained. For emulsions of medical grade quality, the following additional steps are performed, although this was not done and is not necessary for the emulsions shown in, and, conclusions drawn from, Tables 1 and 2. The emulsion was centrifuged at 400 RPM for 30 minutes, to remove dust, and the bottom 10% discarded. This discarding is merely a conservative practice since there is no reason to think the discarded 10% was any different than the other 90%, certainly not in PFC or surfactant content. The top 90% was filtered through a 0.45 micron filter into a sterilizable bottle which was then crimp-sealed and sterilized for 15 minutes at 120°–121° C. The bottle was cooled while swirling. The emulsion is still single phase and looks the same as before sterilizing.

Laser light scattering shows that the average particle size is less than 0.1 micron (both before and after sterilization) with essentially no particles above 0.3 micron.

Table 1 below shows the Cloud Point of 10% PFC emulsions made as above with a blend of surfactant 2 of $\bar{n}=8.5$ (range approximately 7–11) and surfactant 3 of $n=20$ (range approximately 13–25). In the Table, solubility parameter (SP) is the amount of PFC per gm of surfactant and is a measure of the effectiveness of the surfactant.

TABLE 1

| | Total gms Surfactant | Weight Fraction Surfactant 3 | PFC (10%) | Cloud Point-°C. | SP |
|---|---|---|---|---|---|
| A | .0225 | .058 | F-DMA | 31 | 8.8 |
| B | .0231 | .10 | F-DMA | 35.5 | 8.6 |
| C | .0256 | .17 | F-DMA | 43.6 | 7.7 |
| D | .0271 | .24 | F-DMA | 50.0 | 7.0 |
| E | .0271 | .018 | F-MA | 42.2 | 7.6 |
| F | .0254 | .17 | F-Decalin | 41.0 | 7.5 |

It is apparent from the above that, with a given PFC, higher values of $\bar{n}$ (more surfactant 3) give higher cloud points (a wider microemulsion range), which is advantageous, but also lowers the solubilization parameter, i.e., less PFC can be incorporated and still obtain a microemulsion.

It should be noted that it is almost essential that the microemulsion have a broad single phase range with a cloud point of at least 45° C.. A patient with a 105° F. fever is at 40° C. and it would be fatal for the emulsion within the patient to separate into two phases. It should also remain single phase at 20° C., slightly below room temperature, to facilitate normal, everyday storage and handling.

A series of 12.5% F-DMA emulsions were made up with a surfactant the same as above except that $\bar{n}=8.5$ (range=7-11). Varying amounts of surfactant were used from 1 to 3.5%. The single phase temperature range was observed. This phase appears like water and has a viscosity of about 1.5 cp. At temperatures above the cloud point, the emulsion quickly becomes much more viscous and then two phases. Below the cloud point, and as the amount of surfactant drops below a certain minimum level, the emulsion again becomes two phases. The minimum temperature evaluated was 20° C.

TABLE 2

| | Percent Surfactant | One Phase Range - °C. | SP |
|---|---|---|---|
| A | 3.5 | 20-23.5 | 7.1 |
| B | 2.85 | 20-26.5 | 8.8 |
| C | 2.25 | 20-28 | 11.1 |
| D | 1.85 | 20-30 | 13.5 |
| E | 1.50 | 30-32.8 | 16.7 |
| F | 1.30 and under | Two Phase | |

Note that although the one-phase range is not as high as in Table 1, the solubilization parameter is much higher. Using a higher $\bar{n}$ in the emulsions of Table 2, the results could be made to approach those in Table 1.

Although Table 2 shows a minimum single phase temperature of 20° C., this is only because no lower measurements were made and they are indeed single phase down to 10° C., often 5°-10° C. Actually, my emulsions (e.g., Emulsion B, Table 2) can be made, by raising the $\bar{n}$ to 10-12, with the exceedingly good range of 20°-45° C., often 5°-50° C. This is to be contrasted with the range of 35°-40° C. disclosed in Example 1 of the '843 patent of Chabert et al. Also, Chabert et al achieve a solubility parameter of only about 6, which is lower than almost all of my emulsions.

As noted above, my microemulsions have much lower toxicity than the "very toxic" microemulsions of Chabert et al. My emulsions have a typical LD50 of more than 20 ml. per kilogram which, while not as good as we would like to have, would be described as not very toxic. In addition, my emulsions show little or no crenation, hemolysis, or aggregation. These characteristics, combined with the very small particle size possible with my emulsions, which makes them stable for many months, make my emulsions an order of magnitude advance in perfluorocarbon medical emulsions.

My surfactant can be made by known procedures, e.g., by ethoxylation or propoxylation of the appropriate alcohol. Such a procedure is disclosed in the above-mentioned Chabert et al patent. This procedure, however, does not give a surfactant as pure or as well defined as the four-step procedure I use, which is substantially that disclosed by B. Castro et al in Medicine et armees, Paris, 1984, 12, 2, and in *Tetrahedron*, 39(8) 1313, (1983).

This procedure involves the conversion of the appropriate glycol to the monophosphonium salt, followed by reaction of this salt with the sodium salt of the fluorinated alcohol. The specific procedure is described as follows, in which, for illustrative purposes, it will be assumed that ethylene oxide is the glycol i.e., $R'=C_2H_4$, that m in the surfactant formula is 6 or 8 as noted, and that R is $CF_3$. Unless otherwise specified, the reactants, and other materials are obtained from normal commercial sources.

1. Preparation of Alcohol-$CF_3(CF_2)_7C(CF_3)_2OH$

Ethyl ether and tetrahydrofuran (THF) are dried with lithium aluminum hydride immediately prior to use, and 300 ml. of each are added to a 2 l. flask which has been previously purged with $N_2$. The flask is equipped with a mechanical stirrer, addition funnel, and is cooled to $-78°$ C. with a dry ice/acetone bath; 181 ml. of a 3M solution of $C_2H_5MgBr$ in ether (543 mM.) is added to the additional funnel. 2 ml. of the solution are added to the flask to remove any traces of $H_2O$. The exclusion of water is essential to the reaction.

452 millimoles (mM.) of $C_8F_{17}I$ is dissolved in 150 ml. of dry THF and added to the flask, and the contents of the flask are stirred for 5 minutes to reach temperature equilibrium. The remaining 179 ml. of the 3M EtMgBr solution is slowly added to the flask over 1.5 hours while keeping the temperature of the reaction mixture below $-65°$ C. The mixture is then stirred for another 3 hours at $-78°$ C. The reaction product is $C_8F_{17}MgBr$ plus by-product $C_2H_5I$.

Hexafluoroacetone (589 mM.) is condensed with liquid nitrogen and added to the reaction mixture at $-78°$ C. The reaction mixture is then allowed to warm slowly to room temperature with constant stirring. The solvents and any unreacted $C_3F_6O$ are removed by vacuum leaving a solid yellow residue of crude Mg salt of the fluorinated alcohol. The solid is mixed with 500 ml. of 1.2N HCl and the resulting lower organic layer, containing the heavier fluorinated material, is separated and set aside.

The remaining aqueous HCl layer is washed twice with 250 mls. ether; the two ether extracts are combined with the organic layer previously set aside and the organic material is then washed, first with 150 ml. brine, then with 150 ml. water. The washed organic is dried over $MgSO_4$, after which the ether is removed under vacuum to leave a liquid residue of fluorinated alcohol. The residue is treated with 70 ml. of concentrated sulfuric acid to remove any water of hydration from the alcohol, for otherwise it would not be possible to form the sodium salt of the alcohol in the next reaction step.

The deep red alcohol-containing lower layer is distilled at 1 mm Hg and 16 g. (48.4% alcohol) of a first fraction (B.Pt. 36°-44° C.) and 53 g. (93.5% alcohol) of a second fraction (44°-47° C.) were taken off. The fractions were combined and redistilled at 25 mm Hg. to yield 41 g. of an 87°-91° C. fraction which is 95.7% $CF_3(CF_2)_7C(CF_3)_2OH$.

2. Preparation of Alcohol Sodium Salt

Sodium metal is added to methanol to make a 3.3M solution of $CH_3OH$. Next, 41.2 mM. of $C_6F_{13}C(CF_3)_2OH$ is added to a 500 ml. flask equipped with a stirrer and maintained at 0° C. This $C_9$ alcohol is made in the manner described in Section 1 above for a $C_{11}$ alcohol. The $C_9$ alcohol is cheaper and therefore preferred, but both are technically suitable. Next, 12.5 ml. of the above $CH_3ONa$ solution (41.2 mM) is added without stirring. After 30 minutes of stirring at 0° C., the mixture is allowed to warm to room termperature, after which stirring continues for 4 more hours. Next, the $CH_3OH$ solvent is removed under vacuum and the resulting solid, the $C_6F_{13}C(CF_3)_2ONa$ salt, is subjected to vacuum for an additional hour to insure complete removal of solvent and any other volatiles. After this 1 hour period, 100 ml. of dioxane is added to the flask.

3. Preparation of Glycol Phosphonium Salt $H(OCH_2CH_2)_nOP(NMe_2)_3PF_6$

To a 500 ml. flask equipped with a stirrer is added 50 mM. polyethylene glycol (PEG) (nominal mol. wt.=400, n=9), 125 mM. $CCL_4$ and 40 ml. THF. The flask is cooled to about $-40°$ C. and 50 mM of 85% hexamethylphosphorous triamide [$(CH_3)_2N]_3P$ dissolved in 10 ml. THF is added to the flask over a period of 1.5 hours, after which the reaction mixture is stirred at $-40°$ C. for 1 hour.

The contents of the flask are poured into 150 ml. water. Two layers form, an aqueous layer containing the product, the monophosphonium salt of PEG, $H(OCH_2CH_2)_nOP(NMe_2)_3Cl^-$, and an organic layer. The organic layer is washed with 100 ml. water and then discarded, with the aqueous extract being combined with the other aqueous phase. The resulting aqueous phase is washed with 100 ml. ether and the ether extract is discarded.

An aqueous solution of 100 mM. of $KPF_6$ is added to the aqueous phase; immediately the aqueous phase turns milky because the reaction product is not entirely soluble. The suspension is twice extracted with 150 ml. $CH_2Cl_2$ and the extracts, containing the product, are combined and dried over $MgSO_4$. The methylene chloride solvent is removed under vacuum and 28.1 g. of a viscous oily liquid is obtained. This oily liquid is the phosphonium salt $H(OCH_2CH_2)_nOP(NMe_2)_3PF_6$.

IR analysis shows a peak at 1640 cm$^{-1}$ which indicates the salt contains water. Absence of water is mandatory to insure a high yield in the reaction of this salt with the fluorinated alcohol sodium salt. To remove this water, the salt is redissolved in $CH_2Cl_2$, 2 g. silica gel/g. salt is added, and the slurry is stirred for 5 hours, and then filtered. The filtrate is rinsed with $CH_2Cl_2$ after which the solvent is removed under vacuum. The salt obtained is now substantially free of water.

The above procedure varies slightly with PEGs of nominal molecular weights 600, 800 and 1000. Rather than obtaining a single, viscous oily layer, after the vacuum removal of the $CH_2Cl_2$, two layers are obtained. The upper layer, which is 80-95% by volume of the total, is the viscous oily product, and it is separated from the lower layer which is discarded. Thereafter, the procedure is the same as described above.

Preparation of Surfactant $C_6F_{13}$ $C(CF_3)O_2-(CH_2CH_2O)_nH$

Next, the phosphonium salt described above (32.4 g., 45.8 mM) dissolved in 50 ml. dioxane is added to the flask containing the alcohol, sodium salt, and the reaction mixture is heated at 60° C. for 24 hours. The mixture is cooled to room temperature and then 200 ml. of 1.2N HCl is added. The resulting solution is twice extracted with 150 ml. ether, the ether extracts are combined, and the combined ether product is dried over $MgSO_4$. Removal of the ether under vacuum yielded 25.8 g. of crude surfactant. The major impurity is the perfluoroalcohol which is partially removed by heating at 60° C. in vacuo (.001 mm Hg) and then completely removed by passing this product through a silica gel column. The yield of surfactant is 50.9 mol percent based on perfluoroalcohol.

In the PEG's higher than nominal molecular weight of 400 as used above, it is usually possible to remove the alcohol from the curde surfactant product by heating to 65°-70° C. under high vacuum with a cold finger, thus avoiding the silica gel treatment. It is essential to a good surfactant that all alcohol and any volatiles be removed from the surfactant.

The polyethylene or propylene glycols are widely available commercially in different values for n. For example PEG 400 would have an $\bar{n}$ of 9.1, since each $C_2H_4O$ unit has a molecular weight of 44. Likewise, PEG 1000 would have an $\bar{n}$ of 22.7. The actual $\bar{n}$ varies somewhat from these nominal values.

There is, of course, a range of n in any commercial product. Thus a typical PEG 400 had the following composition, based on GC area

| n | % of PEG 400 |
|---|---|
| 5 | 7.0 |
| 6 | 11.3 |
| 7 | 19.2 |
| 8 | 23.5 |
| 9 | 22.5 |
| 10 | 16.5 |

Likewise a PEG 800 had the following distribution:

| n | % of PEG 800 |
|---|---|
| 13 | 2.0 |
| 14 | 3.8 |
| 15 | 6.1 |
| 16 | 9.0 |
| 17 | 11.9 |
| 18 | 13.9 |
| 19 | 14.5 |
| 20 | 13.6 |
| 21 | 11.4 |
| 22 | 8.3 |
| 23 | 4.6 |

The fractions can be separated and used as such, but this is not essential. However, when using the PEG as is, care should be taken to note that the n distribution in the surfactant product will be slightly different than in the PEG.

Thus the PEG 400 shown above had the following distribution in surfactant made therefrom.

| n | % |
|---|---|
| 5 | 16.3 |
| 6 | 17.9 |
| 7 | 26.3 |
| 8 | 18.5 |
| 9 | 11.3 |
| 10 | 9.7 |

The reason for this difference between the PEG and the surfactant is believed to be less than perfect extraction of the surfactant from the dioxane with the ether (Step 4 above). However, the correlation between the initial and final distribution is easy to determine and thus represents no serious problem.

I claim:

1. A microemulsion comprising a perfluorocarbon dispersed in water and a surfactant having the formula

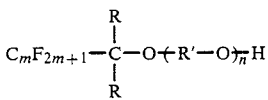

where m is 4–12, R is independently selected from $C_{1-5}$ alkyl and fluoroalkyl, R" is selected from the group of $C_2H_4$ and $C_3H_6$ and $\overline{n}$ is 5–30.

2. A microemulsion according to claim 1 containing 10–50% perfluorocarbon and 1–10% surfactant.

3. A microemulsion according to any one of claims 1 and 2 having a single phase range of at least 20° C. to 45° C.

4. A microemulsion according to any one of claims 1, 2 and 3 wherein R is $CH_3$ or $CF_3$, R" is $C_2H_4$ and n is 7–13.

5. A microemulsion according to any one of claims 1–4 additionally containing a therapeutic agent.

* * * * *